United States Patent
Hisatsu

(10) Patent No.: US 12,274,584 B2
(45) Date of Patent: Apr. 15, 2025

(54) ULTRASOUND DIAGNOSTIC DEVICE AND IMAGE PROCESSING METHOD, CONFIGURED TO APPLY TWO-DIMENSIONALLY DISTRIBUTED WEIGHTS

(71) Applicant: FUJIFILM Healthcare Corporation, Kashiwa (JP)

(72) Inventor: Masanori Hisatsu, Chiba (JP)

(73) Assignee: FUJIFILM Corporation, Tokyo (JP)

( * ) Notice: Subject to any disclaimer, the term of this patent is extended or adjusted under 35 U.S.C. 154(b) by 410 days.

(21) Appl. No.: 17/752,011

(22) Filed: May 24, 2022

(65) Prior Publication Data

US 2022/0378404 A1 Dec. 1, 2022

(30) Foreign Application Priority Data

May 31, 2021 (JP) ................. 2021-091041

(51) Int. Cl.

| A61B 8/00 | (2006.01) |
| G01S 15/89 | (2006.01) |
| G06T 5/50 | (2006.01) |
| G06T 5/70 | (2024.01) |
| G06T 7/00 | (2017.01) |

(52) U.S. Cl.
CPC ............ *A61B 8/5238* (2013.01); *G06T 5/50* (2013.01); *G06T 7/0012* (2013.01); *G06T 2207/10132* (2013.01); *G06T 2207/20221* (2013.01)

(58) Field of Classification Search
CPC ....... A61B 8/5238; G06T 5/50; G06T 7/0012; G06T 2207/10132; G06T 2207/20221
See application file for complete search history.

(56) References Cited

U.S. PATENT DOCUMENTS

| 6,432,054 B1 * | 8/2002 | Ustuner | G01S 7/52046 600/443 |
| 2004/0122321 A1 | 6/2004 | Alexandru | |

(Continued)

FOREIGN PATENT DOCUMENTS

| JP | H 10-305032 A | 11/1998 |
| JP | 2015-213673 A | 12/2015 |

(Continued)

OTHER PUBLICATIONS

Seo, Chi Hyung, and Jesse T Yen. "Sidelobe suppression in ultrasound imaging using dual apodization with cross-correlation." IEEE transactions on ultrasonics, ferroelectrics, and frequency control vol. 55, 10 (2008): 2198-210. doi:10.1109/TUFFC.919 (Year: 2008).*

(Continued)

*Primary Examiner* — Chineyere Wills-Burns
*Assistant Examiner* — Lucius Cameron Green Allen
(74) *Attorney, Agent, or Firm* — Paul Teng

(57) ABSTRACT

A first synthesis unit generates a first synthetic image by applying a first weight distribution to a plurality of subimages and then synthesizing the sub-images. A second synthesis unit generates a second synthetic image by applying a second weight distribution to the plurality of subimages and then synthesizing the sub-images. A generation unit generates a display image based on the first synthetic image and the second synthetic image.

14 Claims, 9 Drawing Sheets

(56) References Cited

U.S. PATENT DOCUMENTS

| | | | |
|---|---|---|---|
| 2007/0285315 A1* | 12/2007 | Davis | H01Q 21/22 |
| | | | 342/377 |
| 2013/0336088 A1* | 12/2013 | Umezawa | G01S 15/89 |
| | | | 367/8 |
| 2016/0066888 A1* | 3/2016 | Yao | A61B 8/481 |
| | | | 600/431 |
| 2016/0324505 A1* | 11/2016 | Maeda | G06T 5/73 |
| 2017/0238908 A1* | 8/2017 | Hisatsu | G01S 15/8997 |
| 2018/0021013 A1* | 1/2018 | Suzuki | G01S 15/8997 |
| | | | 600/459 |
| 2019/0209133 A1 | 7/2019 | Takahashi et al. | |
| 2019/0380684 A1* | 12/2019 | Insana | A61B 8/5207 |

FOREIGN PATENT DOCUMENTS

| | | |
|---|---|---|
| JP | 2016-077442 A | 5/2016 |
| JP | 6059782 B1 | 1/2017 |
| JP | WO 2016/129376 A1 | 11/2017 |
| JP | 2019-118715 A | 7/2019 |
| WO | WO 2016/060017 A1 | 4/2016 |

OTHER PUBLICATIONS

Japanese official action dated Apr. 2, 2024 (and machine translation thereof in English language) in connection with Japanese Patent Application No. 2021-091041.

Chi Hyung Seo, et. al., "Sidelobe Suppression in Ultrasound Imaging Using Dual Apodization with Cross-Correlation", IEEE UFFC, vol. 55, No. 10, pp. 2198-2210 (2008).

Japanese official action dated Nov. 28, 2023 (and machine translation thereof in English language) in connection with Japanese Patent Application No. 2021-091041.

* cited by examiner

ULTRASOUND DIAGNOSTIC DEVICE AND IMAGE PROCESSING METHOD, CONFIGURED TO APPLY TWO-DIMENSIONALLY DISTRIBUTED WEIGHTS

CROSS REFERENCE TO RELATED APPLICATION

This application claims priority to Japanese Patent Application No. 2021-091041 filed on May 31, 2021, which is incorporated herein by reference in its entirety including the specification, claims, drawings, and abstract.

TECHNICAL FIELD

The present disclosure relates to an ultrasound diagnostic device and an image processing method, and particularly to an ultrasound diagnostic device and an image processing method for processing an image according to a synthetic transmit aperture method.

BACKGROUND

JP 2016-77442 A (Document 1) and JPWO 2016-129376 (Document 2) describe an ultrasound diagnostic device that executes a synthetic transmit aperture method. In the synthetic transmit aperture method (more precisely, the synthetic transmit aperture method using a virtual source), a transmission focal point formed in a living body is regarded as the virtual source. Specifically, when a reception unit generates or calculates delay data for phase-alignment and summing (delay and summing), a propagation time of a spherical wave from the virtual source to each reception point is taken into consideration. By synthesizing a plurality of sub-images (a plurality of low resolution images) generated by a plurality of times of transmission and reception, a synthetic image (a high resolution image) is generated.

Prior to synthesis of the plurality of sub-images, a weight distribution is applied (typically, by multiplication) to each sub-image. The weight distribution includes a plurality of weights distributed two-dimensionally. By applying the weight distribution, a gain in the synthetic image is spatially uniformized, and an invalid portion included in each sub-image is excluded. Documents 1 and 2 do not describe that the plurality of weight distributions are applied in parallel to the same sub-image.

JP 2015-213673 A (Document 3) and Chi Hyung Seo, et. al., Sidelobe Suppression in Ultrasound Imaging Using Dual Apodization with Cross-Correlation, IEEE UFFC, Vol. 55, No. 10, 2008. (Document 4) disclose that a plurality of weighting functions are applied in parallel to a beam data string. Documents 3 and 4 do not disclose a configuration for synthetic transmit aperture.

SUMMARY

An object of the present disclosure is to improve the quality of a display image when the display image is generated according to a synthetic transmit aperture method. Alternatively, an object of the present disclosure is to reduce unnecessary components such as sidelobe components and artifact components when a display image is generated according to the synthetic transmit aperture method.

An ultrasound diagnostic device according to the present disclosure includes: a reception unit that generates a plurality of sub-images for synthetic transmit aperture; a first synthesis unit that generates a first synthetic image by applying a first weight distribution to the plurality of sub-images and then synthesizing the sub-images; a second synthesis unit that generates a second synthetic image by applying a second weight distribution different from the first weight distribution to the plurality of sub-images and then synthesizing the sub-images; and a generation unit that generates a display image based on the first synthetic image and the second synthetic image.

An image processing method according to the present disclosure includes: a step of generating a plurality of sub-images for synthetic transmit aperture; a step of generating a first synthetic image by applying a first weight distribution to the plurality of sub-images and then synthesizing the sub-images; a step of generating a second synthetic image by applying a second weight distribution different from the first weight distribution to the plurality of sub-images and then synthesizing the sub-images or by synthesizing the plurality of sub-images; a step of calculating a similarity set based on the first synthetic image and the second synthetic image; and a step of adjusting a gain of the first synthetic image based on the similarity set to generate a display image.

BRIEF DESCRIPTION OF DRAWINGS

Embodiment(s) of the present disclosure will be described based on the following figures, wherein.

DESCRIPTION OF EMBODIMENTS

Figure 1:
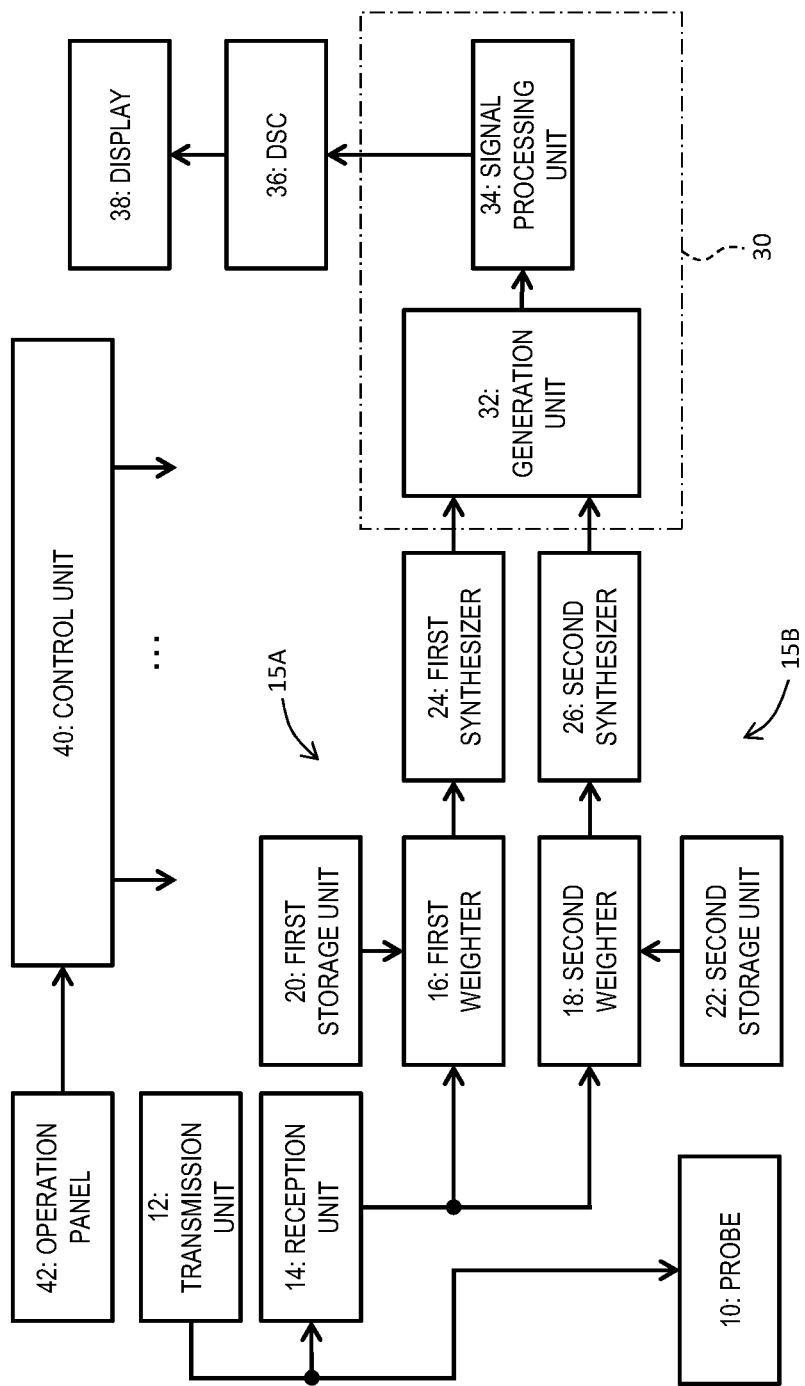
FIG. 1 is a block diagram showing an ultrasound diagnostic device according to a first embodiment.

Hereinafter, embodiments will be described with reference to the drawings.

(1) Outline of Embodiments

An ultrasound diagnostic device according to an embodiment includes a reception unit, a first synthesis unit, a second synthesis unit, and a generation unit. The reception unit generates a plurality of sub-images for synthetic transmit aperture. The first synthesis unit applies a first weight distribution to the plurality of sub-images and then synthesizes the sub-images to generate a first synthetic image. The second synthesis unit applies a second weight distribution different from the first weight distribution to the plurality of sub-images and then synthesizes the sub-images to generate a second synthetic image. The generation unit generates a display image based on the first synthetic image and the second synthetic image. The reception unit corresponds to a receiver. The first synthesis unit corresponds to a first synthesizer. The second synthesis unit corresponds to a second synthesizer. The generation unit corresponds to a generator. Each weight distribution is a two-dimensional weight distribution.

According to the above configuration, the display image can be generated based on the first synthetic image and the second synthetic image which have different properties from each other. Therefore, the quality of the display image can be improved as compared with a case in which a single synthetic image is used as it is for display. For example, as a combination of the first weight distribution and the second weight distribution (a weight distribution pair), a combination that can reduce sidelobes or a combination that can reduce artifacts may be adopted. A plurality of weight distribution pairs may be prepared, and a specific weight distribution pair may be selected from the plurality of weight distribution pairs depending on circumstances. In the embodiment, since a plurality of weight distributions are applied in parallel to the same sub-image, the spatial resolution and the frame rate are substantially not reduced.

The above image processing is performed based on a synthetic transmit aperture method, and particularly based on a synthetic transmit aperture method using a virtual source. The ultrasound diagnostic device according to the embodiment includes a coordinate transformation unit that transforms an image according to a transmission and reception coordinate system into an image according to a display coordinate system. The sub-image, the synthetic image, and the display image are data before the coordinate transformation or data after the coordinate transformation. In the present specification, the term "image" is defined broadly. The contents of the first weight distribution and the contents of the second weight distribution may be dynamically changed according to a position of a transmission and reception aperture in an electronic scanning direction.

In the embodiment, the generation unit includes a calculator that calculates a similarity set based on the first synthetic image and the second synthetic image, and a gain adjuster that adjusts a gain of one or both of the first synthetic image and the second synthetic image based on the similarity set to generate the display image.

The similarity is an index indicating a probability of being a true component. A correlation coefficient may be used as the similarity. When the display image is generated, an original image that is the source of the display image is one or both of the first synthetic image and the second synthetic image. The gain adjuster increases the gain of the original image when the similarity is high, and decreases the gain of the original image when the similarity is low. Accordingly, it is possible to reduce sidelobe components while preserving the true component.

In the embodiment, the gain adjuster generates the display image by applying the similarity set (a similarity distribution) to the first synthetic image. In this case, the first synthetic image is used as a primary image and the second synthetic image is used as an auxiliary or comparative image. In the embodiment, the second weight distribution is a distribution that causes an increase in the sidelobe components after weighting as compared with the first weight distribution. When the second synthetic image is used as the auxiliary image, a distribution in which all weights are 1 may be adopted as the second weight distribution, or application of the second weight distribution may be omitted when the second synthetic image is generated.

The ultrasound diagnostic device according to the embodiment further includes a detector that applies envelope detection to the display image output from the gain adjuster, and a logarithmic converter that applies logarithmic conversion to the display image output from the detector. By the envelope detection, envelope data are generated based on radio frequency (RF) data. The logarithmic conversion corresponds to a luminance operation according to human visual characteristics.

In the embodiment, the generation unit includes: a first post-processing unit that applies envelope detection and logarithmic conversion to the first synthetic image; a second post-processing unit that applies envelope detection and logarithmic conversion to the second synthetic image; and an adder that adds the first synthetic image output from the first post-processing unit and the second synthetic image output from the second post-processing unit to generate the display image. In this configuration, the first synthetic image and the second synthetic image that have been subjected to the post-processing are added to generate the display image. The first post-processing unit corresponds to a first post-processor. The second post-processing unit corresponds to a second post-processor.

In the embodiment, the first weight distribution has a form (a one-dimensional distribution) shifted to one side in a beam scanning direction at each depth position. The second weight distribution has a form (a one-dimensional distribution) shifted to the other side in the beam scanning direction at each depth position. By using such a weight distribution pair, the artifacts included in the display image can be reduced.

An image processing method according to the present disclosure includes a sub-image generation step, a first synthesis step, a second synthesis step, a calculation step, and a gain adjustment step. In the sub-image generation step, a plurality of sub-images for synthetic transmit aperture are generated. In the first synthesis step, the first weight distribution is applied to the plurality of sub-images, and then the sub-images are synthesized, whereby the first synthetic image is generated. In the second synthesis step, the second weight distribution different from the first weight distribution is applied to the plurality of sub-images, and then the sub-images are synthesized, whereby the second synthetic image is generated. Alternatively, in the second synthesis step, the plurality of sub-images are synthesized to generate the second synthetic image. In the calculation step, the similarity set is calculated based on the first synthetic image and the second synthetic image. In the gain adjustment step, the gain of the first synthetic image is adjusted based on the similarity set, whereby the display image is generated.

In the above configuration, the plurality of sub-images are generated by repeating the transmission of ultrasonic waves to a living body and the reception of reflected waves from the inside of the living body. The first synthetic image and the second synthetic image are generated based on the plurality of sub-images. The first synthetic image is the primary image and the second synthetic image is the auxiliary or comparative image. Therefore, the application of the second weight distribution may be omitted when the second synthetic image is generated. Even if the application of the second weight distribution is omitted, the first synthetic image and the second synthetic image which have different properties from each other can be obtained. The similarity set is generated by comparing those synthetic images, and the display image is generated by applying the similarity set to the first synthetic image.

The above image processing method can be implemented as a function of hardware or a function of software. A program for executing the image processing method may be installed in an information processing apparatus via a portable storage medium or via a network. The concept of the information processing apparatus includes the ultrasound diagnostic device, an ultrasonic image processing device, a computer, and the like. In the information processing apparatus, the above program may be stored in a non-temporary storage medium.

(2) Details of Embodiment

FIG. 1 shows a configuration of the ultrasound diagnostic device according to a first embodiment. The ultrasound diagnostic device is a medical device that is provided in a medical institution or the like and that generates and displays an ultrasonic image based on data obtained by transmitting or receiving ultrasonic waves to or from a subject (a living body). The ultrasound diagnostic device according to the embodiment has a configuration in which the synthetic transmit aperture method using the virtual source is executed.

In FIG. 1, a probe 10 is a portable transmitting and receiving device that contacts a surface of the subject. A transducer array including a plurality of transducers is provided in the probe 10. An ultrasonic beam is formed by the transducer array, and electronic scanning is performed with the ultrasonic beam. Accordingly, a beam scanning plane is formed inside the subject. The electronic scanning with the ultrasonic beam is repeated, whereby the formation of the beam scanning plane is repeated. The beam scanning plane is a two-dimensional data acquisition region. As an electronic scanning method, an electronic linear scanning method, an electronic sector scanning method, and the like are known. A two-dimensional transducer array may be provided in the probe 10, and volume data may be acquired from a three-dimensional space in the living body.

A transmission unit 12 is a transmission circuit that functions as a transmission beam former. A reception unit 14 is a reception circuit that functions as a reception beam former. During transmission, the transmission unit 12 outputs a plurality of transmission signals to the transducer array in parallel. Accordingly, a transmission beam is formed. During reception, when the reflected waves from the inside of the living body are received by the transducer array, a plurality of reception signals are output from the transducer array to the reception unit 14 in parallel.

The reception unit 14 applies phase-alignment and summing (delay and summing) to the plurality of reception signals, thereby generating beam data. The beam data are RF data before envelope detection. The reception unit 14 includes a plurality of A/D converters, a plurality of delayers, and the adder. Actually, parallel reception is executed in the reception unit 14, and the reception unit 14 generates a plurality of pieces of beam data arranged in the electronic scanning direction (the beam scanning direction) per reception.

In the reception unit 14, delay data to be given to each delayer are calculated according to the synthetic transmit aperture method. Specifically, in the calculation of the individual delay data, consideration is given to a propagation time of the transmission wave from a center (a reference position that defines the transmission reference time) of a transmission aperture to the virtual source (a transmission focal point), a propagation time of the reflected wave from a reception point to each transducer, and a propagation time of a spherical wave from the virtual source to the reception point.

As described above, the plurality of pieces of beam data arranged in the electronic scanning direction are generated in parallel for each time of transmission and reception. The plurality of pieces of beam data form one sub-image as a whole. The sub-image can also be referred to as a low resolution image. By repeatedly executing transmission and reception while changing positions of the transmission aperture and a reception aperture, the plurality of sub-images arranged in the electronic scanning direction are generated. The plurality of sub-images have partially overlapping relation with each other. The plurality of sub-images are sequentially output in parallel to a first synthesis unit 15A and a second synthesis unit 15B.

The first synthesis unit 15A and the second synthesis unit 15B each have a configuration according to the synthetic transmit aperture method. Specifically, the first synthesis unit 15A includes a first weighter 16, a first storage unit 20, and a first synthesizer 24. The second synthesis unit 15B includes a second weighter 18, a second storage unit 22, and a second synthesizer 26.

The first weighter 16 applies (specifically, through multiplication) the first weight distribution stored in the first storage unit 20 to each sub-image. Accordingly, a plurality of weighted sub-images are generated. The plurality of weighted sub-images are synthesized in the first synthesizer 24. Accordingly, the first synthetic image is generated. The first synthetic image can also be referred to as a high resolution image. Similarly, the second weighter 18 applies (specifically, multiplication) the second weight distribution stored in the second storage unit 22 to each sub-image. Accordingly, a plurality of weighted sub-images are generated. The plurality of weighted sub-images are synthesized in the second synthesizer 26. Accordingly, the second synthetic image is generated. The second synthetic image can also be referred to as the high resolution image.

The contents of the first weight distribution and the contents of the second weight distribution are different from each other. Each of the contents of the first weight distribution and the contents of the second weight distribution includes a plurality of two-dimensionally distributed weights. Each sub-image is formed by a plurality of two-dimensionally distributed signal values. For each signal value, a weight corresponding to the signal value is multiplied, and the weighted signal value is obtained. Each weight has, for example, a value from 0 to 1.0. An RF signal or an IQ signal (a complex signal) having phase information constitutes a signal value sequence.

In the first embodiment, a generation unit 32 includes a correlation coefficient calculator and the gain adjuster (multiplier). The generation unit 32 generates the display image based on the first synthetic image and the second synthetic image. Specifically, the generation unit 32 calculates a correlation coefficient set as the similarity set based on the first synthetic image and the second synthetic image. Then, the first synthetic image is multiplied by the correlation coefficient set. The multiplication is executed for the purpose of gain adjustment.

In the first embodiment, the first weight distribution and the second weight distribution are determined such that the sidelobes are reduced after the gain adjustment. Actually, a distribution that can reduce the sidelobes is adopted as the first weight distribution. The second weight distribution is a distribution in which a larger number of sidelobe components remain after weighting as compared with the first weight distribution. That is, the degree of restraint action for the sidelobe components in the first weight distribution is larger than the degree of the restraint action for the sidelobe components in the second weight distribution. The first weight distribution is a main distribution, and the second weight distribution is an auxiliary distribution serving as a comparative distribution.

In the first embodiment, a signal processing unit 34 includes the envelope detector and the logarithmic converter. Other circuits may be further provided in the signal processing unit 34. In the first embodiment, the generation unit 32 and the signal processing unit 34 constitute a module 30. A specific configuration example of the module 30 is shown later in FIG. 5.

A digital scan converter (DSC) 36 functions as the coordinate transformation unit. That is, in the DSC 36, data according to the transmission and reception coordinate system are converted into data according to the display coordinate system. In the embodiment, coordinate conversion is applied to the display image in the DSC 36. The display image after the coordinate conversion is sent to a display 38. The display 38 displays the display image after the coordinate conversion. The display image is, for example, a tomographic image. The DSC 36 also has a pixel interpolation function, a frame rate conversion function, and the like, in addition to a coordinate conversion function. Actually, the display 38 displays a moving image including a plurality of display images arranged side by side on a time axis. The display 38 includes an LCD, an organic EL device, and the like.

A control unit 40 controls an operation of each configuration shown in FIG. 1. The control unit 40 is implemented by a CPU that executes the program. The first synthesis unit 15A, the second synthesis unit 15B, the generation unit 32, the signal processing unit 34, and the DSC 36 can each be implemented by a processor. The CPU may function as the first synthesis unit 15A, the second synthesis unit 15B, the generation unit 32, the signal processing unit 34, and the DSC 36.

An operation panel 42 is connected to the control unit 40. The operation panel 42 is an input device including a plurality of buttons, a plurality of knobs, a trackball, a keyboard, and the like. A synthetic transmit aperture condition may be set by a user (a doctor, a examination technician, or the like) using the operation panel 42.

Figure 2:
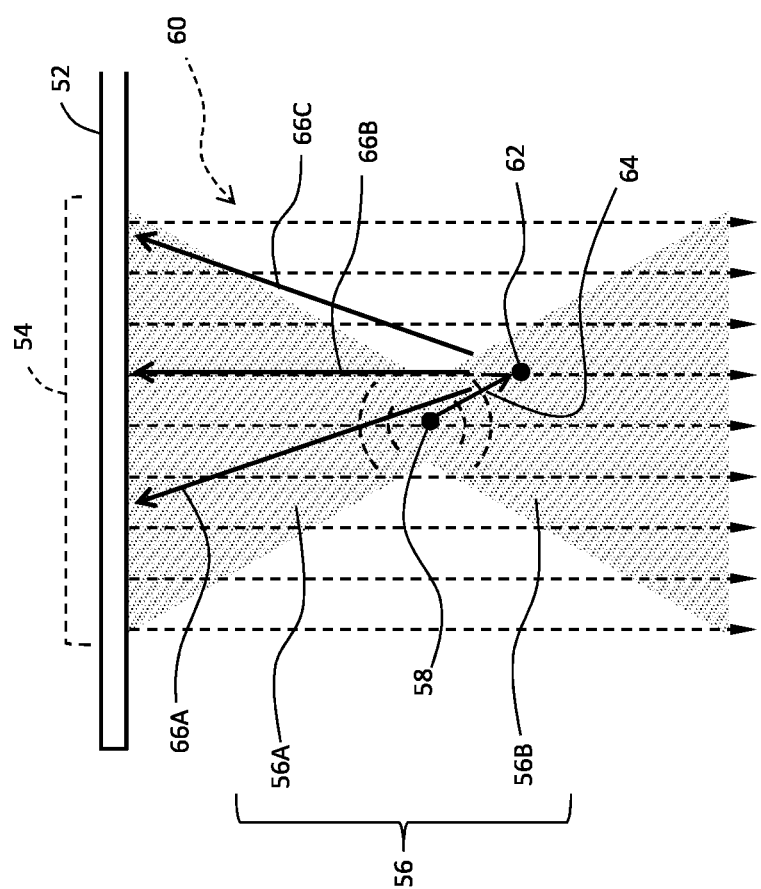
FIG. 2 is a block diagram showing a configuration example of a module shown in FIG. 1.

FIG. 2 schematically shows a method for generating the sub-image. Reference numeral 52 indicates the transducer array. Reference numeral 54 indicates the transmission and reception aperture. The transmission aperture and the reception aperture may be set separately. A plurality of transmission signals having specific delay relation are supplied to the plurality of transducers in the transmission and reception aperture 54. Accordingly, a transmission beam 56 is formed. The transmission beam 56 has a transmission focal point 58. In FIG. 2, a portion expressed in gray is a portion having a sound pressure of a certain value or more.

The transmission beam 56 has an hourglass shape as a whole. In the transmission beam 56, a portion near the transmission focal point 58 is thinned, and a constriction is generated. The transmission beam 56 includes a shallow portion 56A extending upward from the transmission focal point 58 and a deep portion 56B extending downward from the transmission focal point 58.

A reception beam array 60 is formed by executing parallel reception during reception. The reception beam array includes a plurality of reception beams arranged at regular intervals in the electronic scanning direction. When each reception beam is formed, a reception dynamic focus technique is applied. That is, a plurality of reception points (a plurality of reception focal points) are sequentially formed along a depth direction. In FIG. 2, a specific reception point 62 is shown therein.

In order to form the reception focal point at the reception point 62, a first propagation time (see reference numeral 64) of the spherical wave from the transmission focal point (the virtual source) 58 to the reception point 62 and a second propagation time (see, for example, 66A, 66B, 66C) of the reflected wave from the reception point 62 to each transducer are considered according to a virtual source method. Specifically, the delay data for the phase-alignment and summing are calculated by adding the propagation time of the transmission wave from the center of the transmission aperture to the transmission focal point 58, the first propagation time, and the second propagation time.

In one time of transmission and reception, the plurality of pieces of beam data forming one sub-image are generated. By repeatedly executing transmission and reception while shifting the transmission and reception aperture, the plurality of sub-images arranged in the electronic scanning direction are generated per frame.

Figure 3:
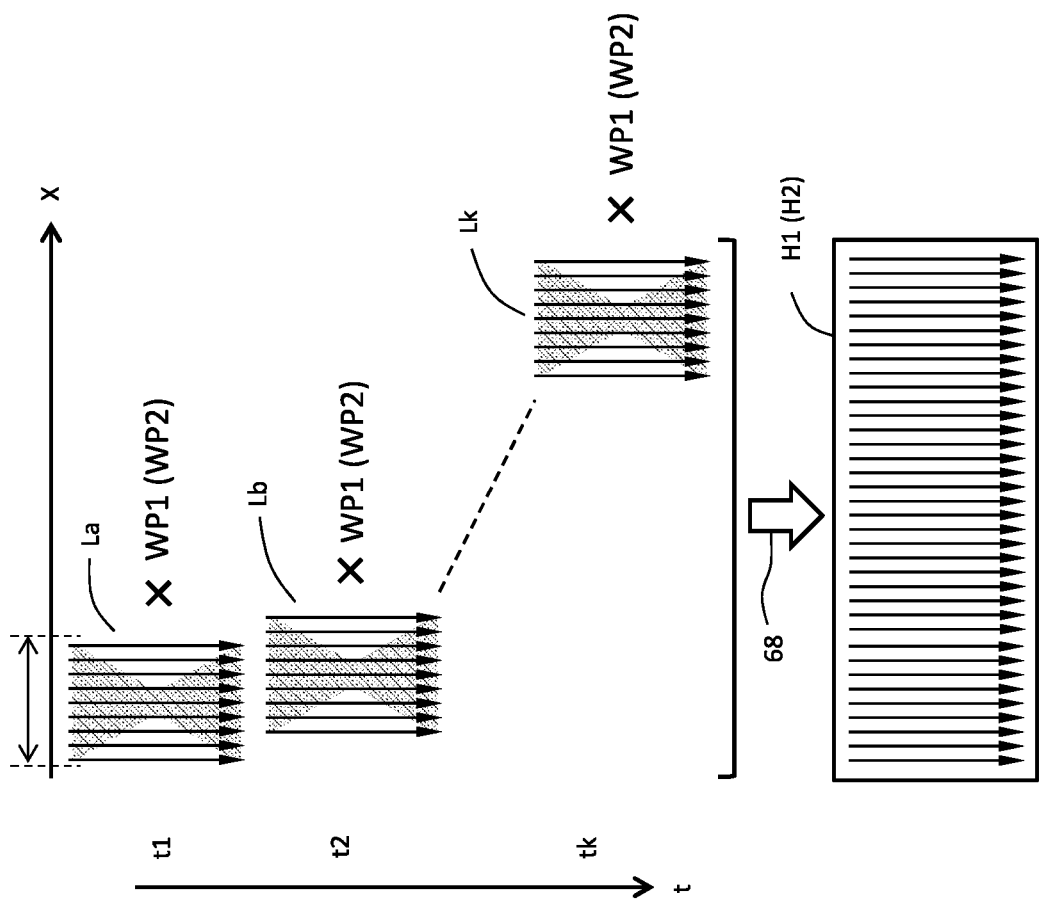
FIG. 3 is a schematic diagram showing generation of sub-images according to a synthetic transmit aperture method.

FIG. 3 schematically shows a synthetic image generation method. A horizontal axis indicates the electronic scanning direction. A vertical axis indicates the time axis.

In the first synthesis unit, each of a plurality of sub-images La to Lk arranged in the electronic scanning direction is multiplied by a weight distribution WP1. A synthetic image H1 is generated by synthesizing the plurality of weighted sub-images. Similarly, in the second synthesis unit, each of the plurality of sub-images La to Lk is multiplied by a weight distribution WP2. A synthetic image H2 is generated by synthesizing the plurality of weighted sub-images.

Figure 4:
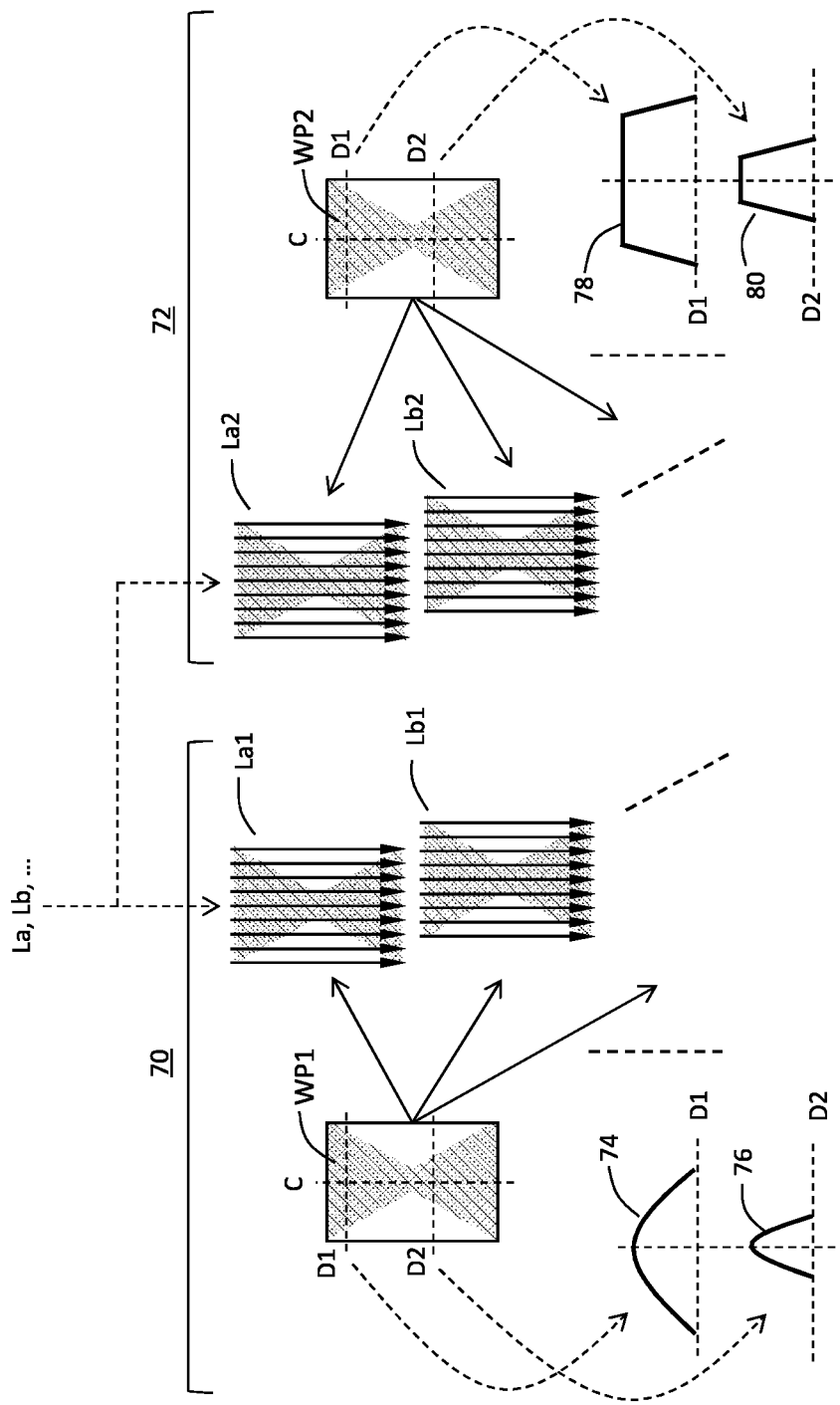
FIG. 4 is a schematic diagram showing generation of synthetic images according to the synthetic transmit aperture method.

FIG. 4 shows multiplication of the plurality of sub-images La, Lb, . . . by the first weight distribution WP1 and the second weight distribution WP2. As a result of the multiplication, a plurality of weighted sub-images La1, Lb1, . . . , and a plurality of weighted sub-images La2, Lb2, . . . are generated.

The first weight distribution WP1 is bilaterally symmetric with respect to a central axis C. Specifically, the first weight distribution WP1 has a mountain-shaped profile at each depth, and a vertex at each depth coincides with the central axis C. A width of the mountain-shaped profile gradually extends upward from the transmission focal point, and a width of the mountain-shaped profile extends downward from the transmission focal point.

For example, a mountain-shaped profile 74 is extended substantially at a depth D1, and the extension of a mountain-shaped profile 76 is restrained at a depth D2. By using such a first weight distribution WP1, the sidelobes generated by the synthetic transmit aperture can be reduced, and a change in luminance of the synthetic image in the depth direction can be smoothed. In each of the profiles 74 and 76, the horizontal axis corresponds to the electronic scanning direction, and the vertical axis indicates a magnitude of the weight.

The second weight distribution WP2 is bilaterally symmetric with respect to the central axis C. Specifically, the second weight distribution WP2 has a trapezoidal profile at each depth. At each depth, a center of the profile coincides with the central axis C. A width of the trapezoidal profile extends upward from the transmission focal point and extends downward from the transmission focal point.

For example, a trapezoidal profile 78 is extended substantially at the depth D1, and the extending of a trapezoidal profile 80 is restrained at the depth D2. By using such a second weight distribution WP2, a synthetic image having more sidelobe components than in the case of using the first weight distribution WP1 can be generated.

Figure 5:
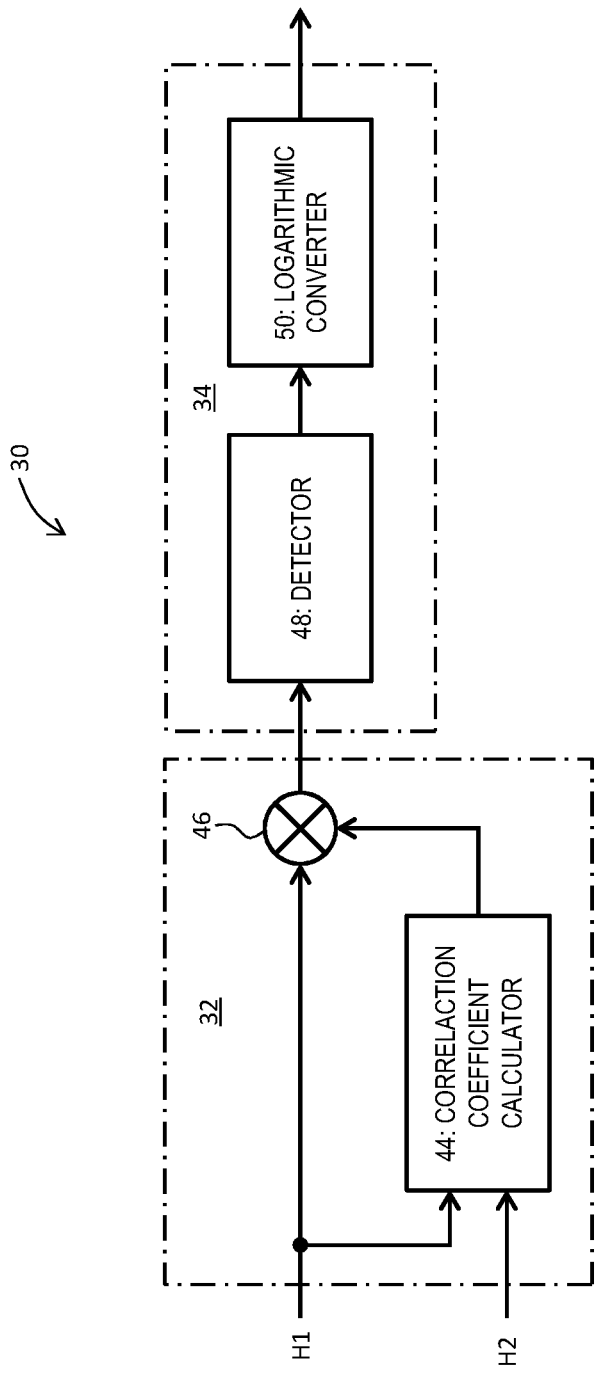
FIG. 5 is a schematic diagram showing sub-image processing according to the first embodiment.

FIG. 5 shows a configuration example of the module 30 shown in FIG. 1. The generation unit 32 includes a correlation coefficient calculator 44 and a multiplier 46. The signal processing unit 34 includes a detector 48 and a logarithmic converter 50.

The correlation coefficient calculator 44 compares a first synthetic image H1 and a second synthetic image H2, thereby calculating a correlation coefficient set as the similarity set. For example, the correlation coefficient ρ (m, n) is calculated according to the following equation (1).

$$\rho(m, n) = \frac{\sum_{k=n-A}^{n+A} HRI1(m, k) \cdot HRI2(m, k)}{\sqrt{\sum_{k=n-A}^{n+A} |HRI1(m, k)|^2 \cdot \sum_{k=n-A}^{n+A} |HRI2(m, k)|^2}} \quad (1)$$

In the above equation (1), HRI1 represents the first synthetic image H1 and HRI2 represents the second synthetic image H2. In addition, m indicates a reception beam number, and n indicates a reception point number (a sample point number) in the depth direction. A defines a size of a reference range in the depth direction. The reference range has a magnitude of 1 in the electronic scanning direction and a magnitude of 2A+1 in the depth direction. A two-dimensional reference range may be set instead of a one-dimensional reference range. The individual synthetic images may be formed by real signals, or the individual synthetic images may be formed by IQ signals (complex signals).

In the multiplier 46, each correlation coefficient is multiplied by a respective one of signal values that form the first synthetic image. Actually, an absolute value of the correlation coefficient calculated according to equation (1) is multiplied. The multiplier 46 functions as the gain adjuster for the first synthetic image H1.

The detector 48 applies envelope detection to an image output from the multiplier 46. RF data are converted to baseband data by envelope detection. The logarithmic converter 50 executes logarithmic conversion on the image after detection output from the detector 48. Accordingly, the image after logarithmic conversion is generated, and the image is output to the DSC as the display image.

According to the first embodiment, the sidelobe components contained in the display image can be effectively reduced without causing a decrease in the frame rate. The plurality of weight distribution pairs may be prepared, and the weight distribution pair to be used may be selected depending on circumstances. Three or more synthetic images may be generated using three or more weight distributions, and the display image may be generated based on the synthetic images.

According to the first embodiment, the unnecessary components (for example, multiple reflection components) other than the sidelobe components can also be reduced. As the generation unit 32, a generator including a machine learning model that generates the display image based on the first synthetic image and the second synthetic image may be provided. In this case, the machine learning model may execute learning such that unnecessary components such as sidelobe components are reduced.

In the first embodiment, the contents of the first weight distribution and the contents of the second weight distribution may be dynamically changed during the electronic scanning of the ultrasonic beam; that is, the electronic scanning of the transmission and reception aperture. During weighting and synthesizing, processing may be executed for each piece of beam data forming the sub-image.

Figure 6:
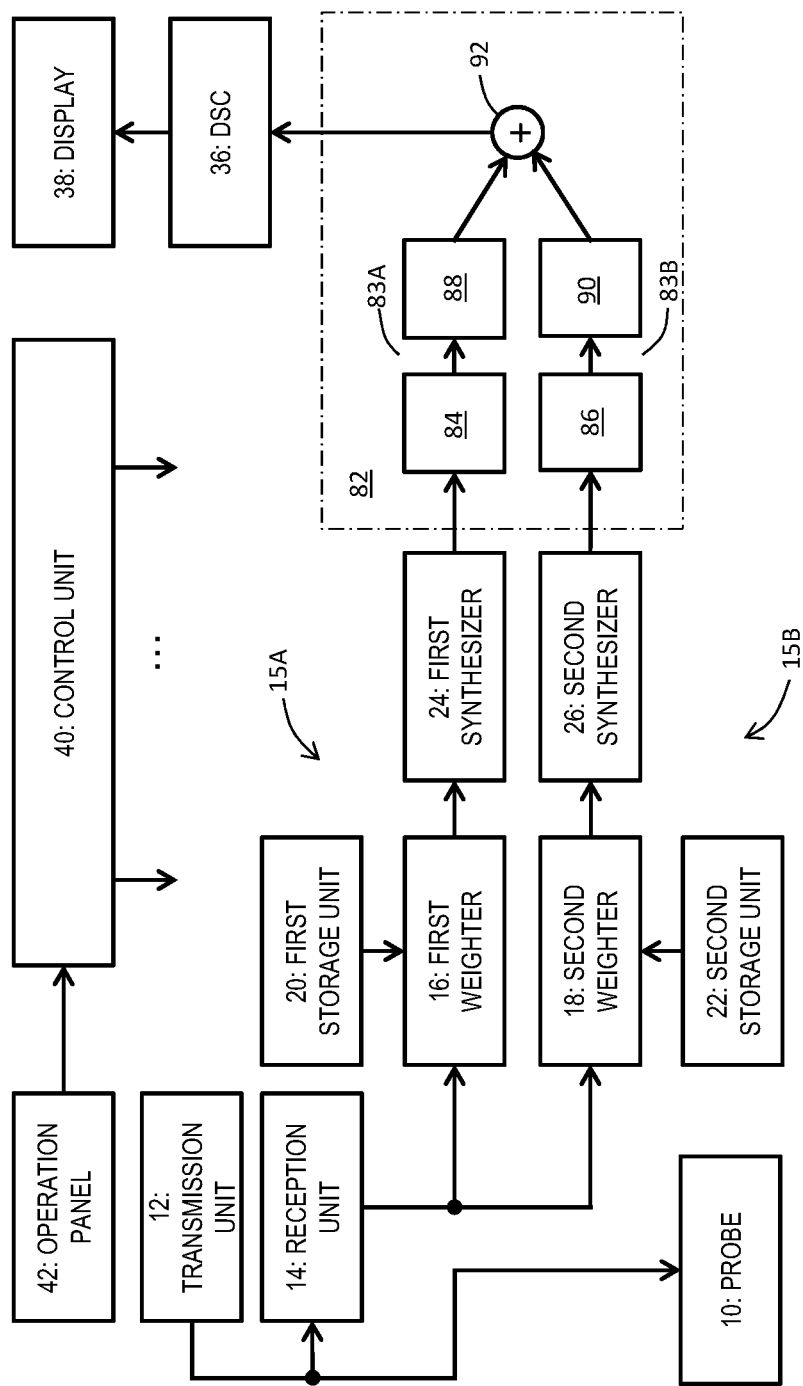
FIG. 6 is a block diagram showing an ultrasound diagnostic device according to a second embodiment.

Next, a second embodiment will be described with reference to FIGS. 6 and 7. FIG. 6 shows a configuration of an ultrasound diagnostic device according to the second embodiment. In FIG. 6, the same reference numerals are assigned to the configurations the same as those shown in FIG. 1, and the description thereof will be omitted. This also applies to FIGS. 6 and 9 to be described later.

In the second embodiment, the first weight distribution for artifact reduction is stored in the first storage unit 20, and the second weight distribution for artifact reduction is stored in the second storage unit 22. The first weighter 16 multiplies the plurality of sub-images by the first weight distribution, and the first synthesizer 24 synthesizes the plurality of weighted sub-images to generate the first synthetic image. Similarly, the second weighter 18 multiplies the plurality of sub-images by the second weight distribution, and the second synthesizer 26 synthesizes the plurality of weighted sub-images to generate the second synthetic image.

A module 82 includes a first post-processing unit 83A including a detector 84 and a logarithmic converter 88, and a second post-processing unit 83B including a detector 86 and a logarithmic converter 90. The module 82 further includes an adder 92. First post-processing (envelope detection and logarithmic conversion) is applied to the first synthetic image. Second post-processing (envelope detection and logarithmic conversion) is applied to the second synthetic image. The synthetic image after the first post-processing and the synthetic image after the second post-processing are added by the adder 92, thereby generating the display image. The display image is sent to the DSC 36.

Figure 7:
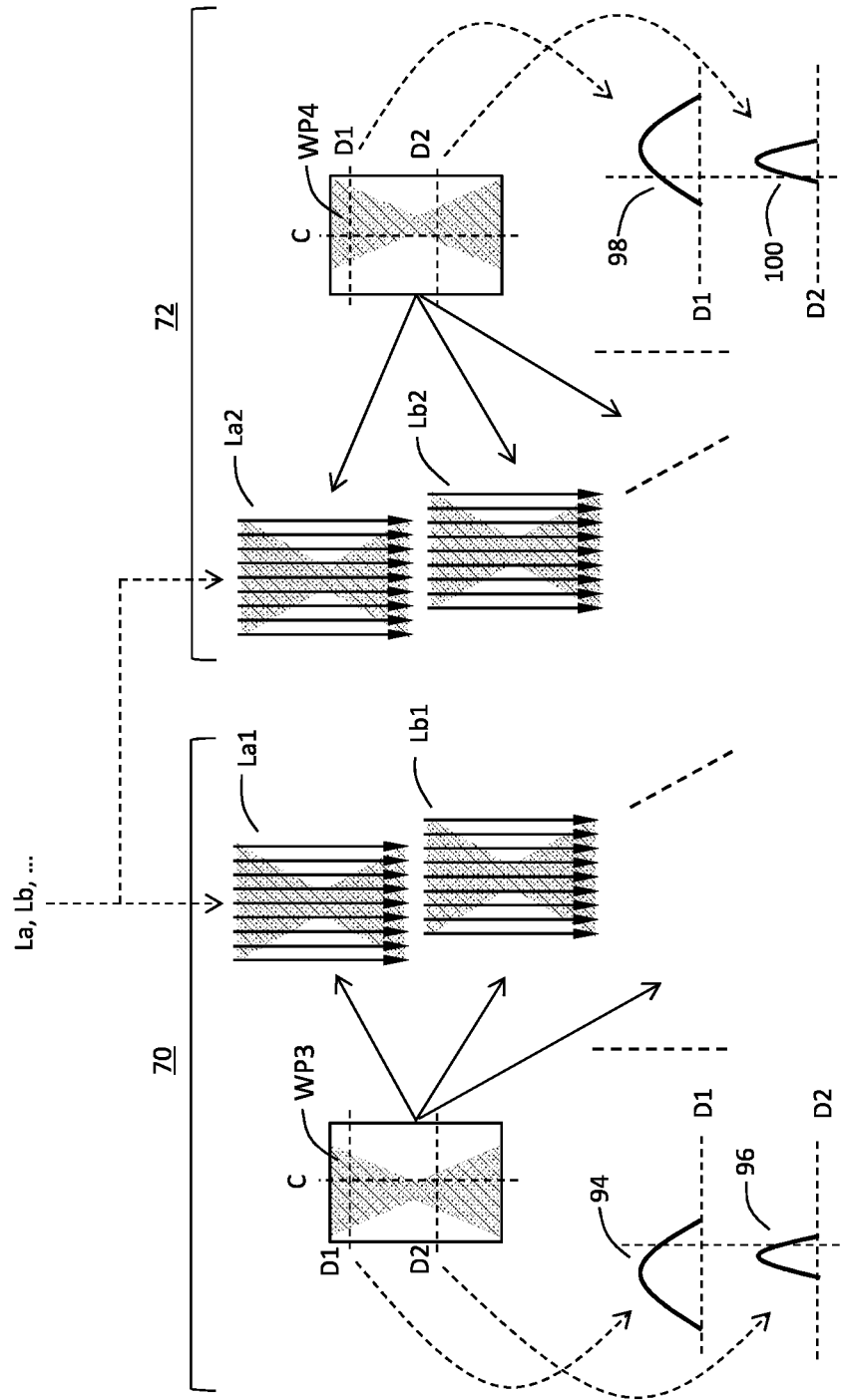
FIG. 7 is a diagram showing sub-image processing according to the second embodiment.

FIG. 7 shows weighting according to the second embodiment. The first weighter multiplies the plurality of sub-images La, Lb, . . . by a first weight distribution WP3. Accordingly, the plurality of weighted sub-images La1, Lb1, . . . are generated. The first synthetic image is generated by synthesizing the weighted sub-images.

The first weight distribution WP3 has a form shifted to one side in the electronic scanning direction with respect to the central axis C. For example, a mountain-shaped profile 94 is displaced to one side in the electronic scanning direction at the depth D1, and a mountain-shaped profile 96 is displaced to one side in the electronic scanning direction at the depth D2. A width of the profile increases as the profile moves upward or downward from the transmission focal point. At each depth, a vertex of the profile is displaced to one side in the electronic scanning direction.

A second weighter multiplies the plurality of sub-images La, Lb, . . . by a second weight distribution WP4. Accordingly, the plurality of weighted sub-images La2, Lb2, . . . are generated. The second synthetic image is generated by synthesizing the weighted sub-images.

The second weight distribution WP4 has a form of being shifted to the other side in the electronic scanning direction with respect to the central axis C. For example, a mountain-shaped profile 98 is displaced to the other side in the electronic scanning direction at the depth D1, and a mountain-shaped profile 100 is displaced to the other side in the electronic scanning direction at the depth D2. The width of the profile increases as the profile moves upward or downward from the transmission focal point. At each depth, the vertex of the profile is displaced to the other side in the electronic scanning direction. The first weight distribution WP3 and the second weight distribution WP2 have an axisymmetric relation with respect to a central axis.

According to the second embodiment, artifacts can be effectively reduced by adding the first synthetic image and the second synthetic image that are generated as described above. In the second embodiment, the first synthetic image after the first post-processing and the second synthetic image after the second synthesis processing are added. Alternatively, after the first synthetic image and the second synthetic image before the post-processing are added to generate the display image, the post-processing (that is, envelope detection and logarithmic conversion) may be applied to the display image. The first synthetic image and the second synthetic image after the envelope detection may be added.

Figure 8:
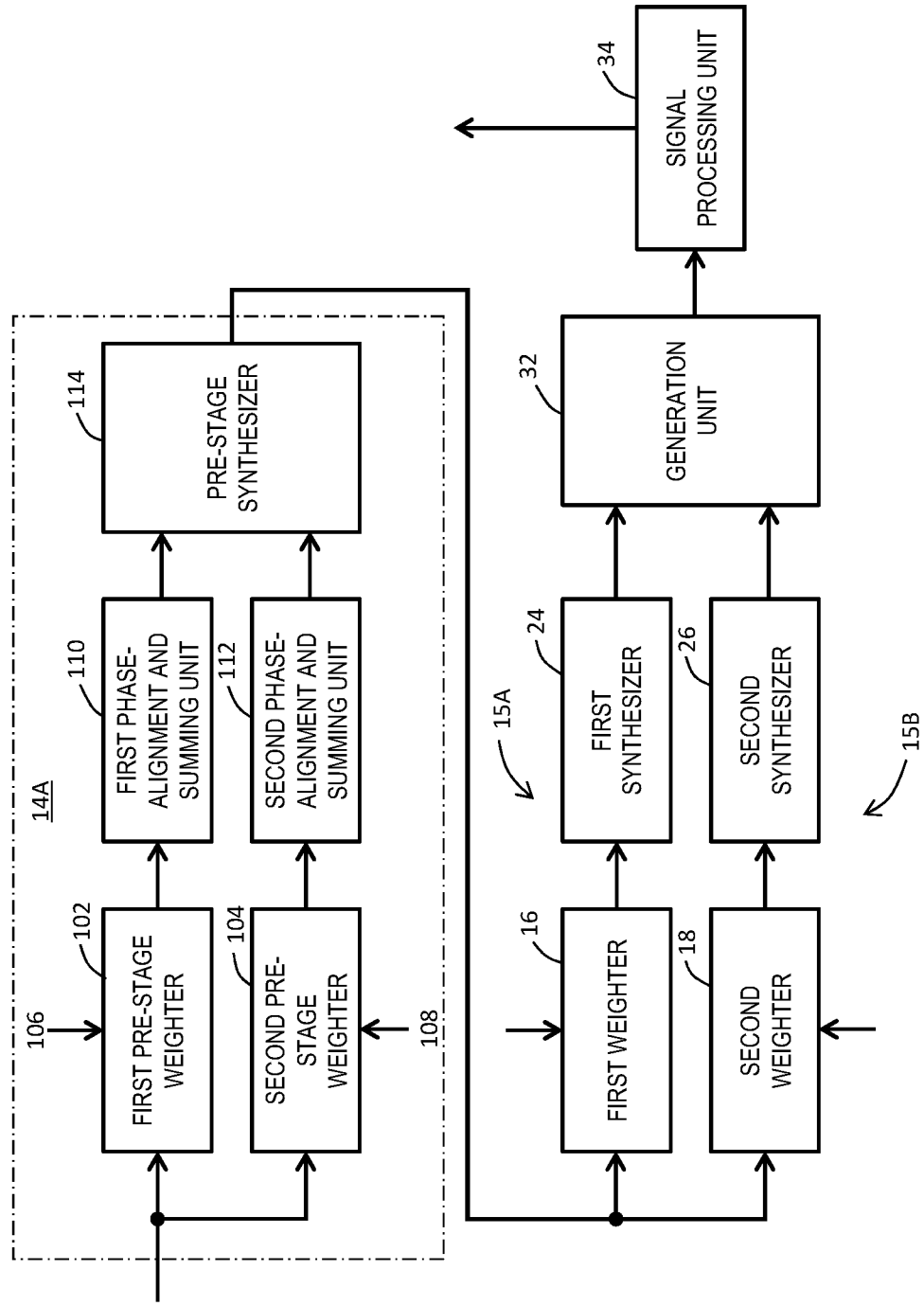
FIG. 8 is a block diagram showing an ultrasound diagnostic device according to a first modification.

FIG. 8 shows a configuration according to a first modification. The first modification corresponds to a modification in which a configuration of the reception unit is modified in the ultrasound diagnostic device according to the first embodiment.

In the first modification, a reception unit 14A includes two processing systems arranged in parallel. That is, the reception unit 14A includes a first pre-stage weighter 102, a second pre-stage weighter 104, a first phase-alignment and summing unit 110, a second phase-alignment and summing unit 112, and a pre-stage synthesizer 114. The first pre-stage weighter 102 multiplies a plurality of reception signals output from the transmission and reception aperture by a first weighting function 106. The second pre-stage weighter 104 multiplies the plurality of reception signals output from the transmission and reception aperture by a second weighting function 108. Each of the first weighting function 106 and the second weighting function 108 include a weight sequence arranged along the electronic scanning direction. The first weighting function 106 and the second weighting function 108 have a form for reducing unnecessary components such as the sidelobe components. For example, examples of these functions are shown in Patent Documents 3 and 4 described above.

In the first phase-alignment and summing unit 110, the plurality of weighted reception signals are subjected to phase-alignment and summing according to a parallel reception method to generate the plurality of pieces of beam data. The plurality of pieces of beam data correspond to a first sub-image. Similarly, in the second phase-alignment and summing unit 112, the plurality of weighted reception signals are subjected to phase-alignment and summing according to the parallel reception method to generate the plurality of pieces of beam data. The plurality of pieces of beam data correspond to a second sub-image. The weighted first sub-image and the weighted second sub-image are synthesized (added) in the pre-stage synthesizer 114. Accordingly, a synthetic sub-image is generated. A plurality of synthetic sub-images are sequentially generated along with the electronic scanning, and the synthetic sub-images are sent in parallel to the first synthesis unit 15A and the second synthetic unit 15B.

According to the first modification shown in FIG. 8, unnecessary components such as the sidelobe components can be further reduced. In this modification, the first pre-stage weighter 102 and the second pre-stage weighter 104 may be operated alternately in a time division manner.

Figure 9:
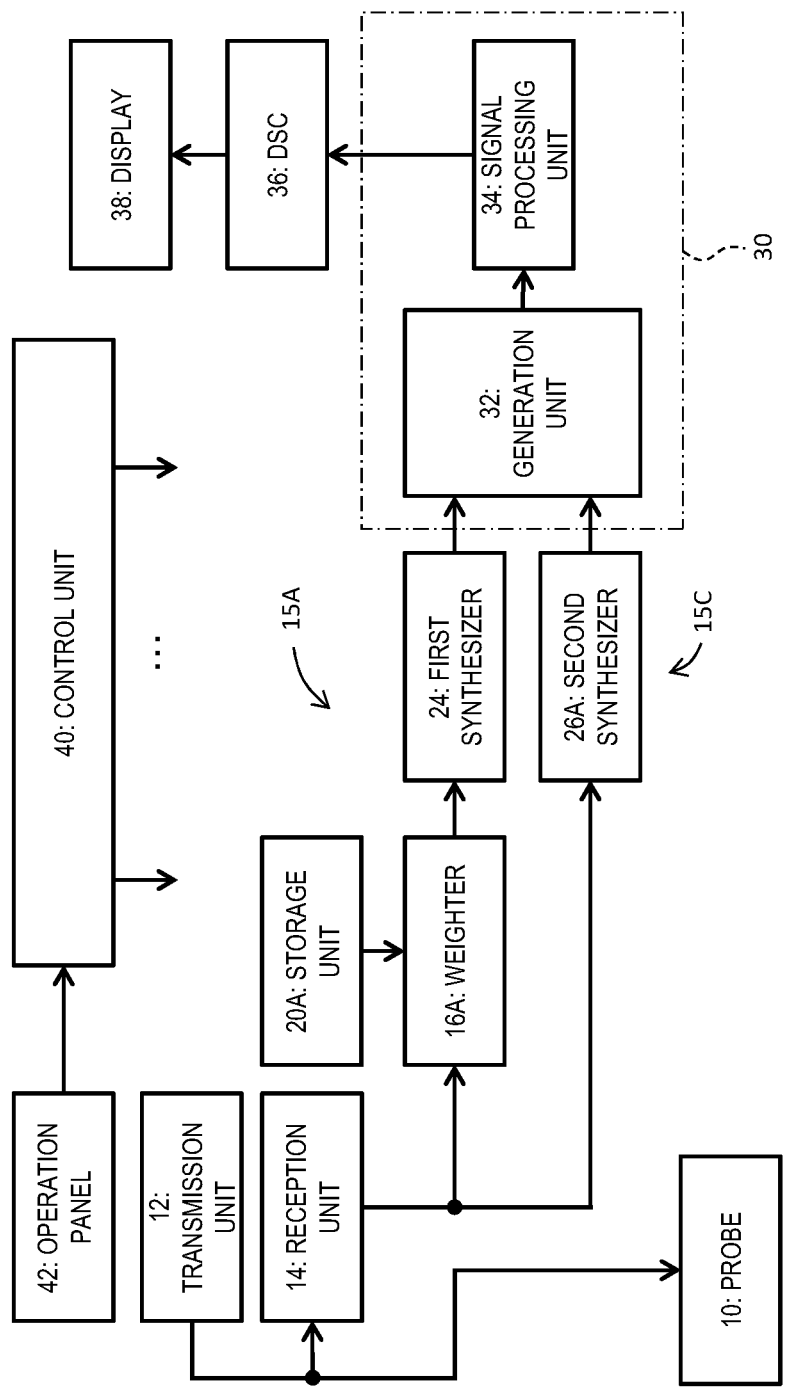
FIG. 9 is a block diagram showing an ultrasound diagnostic device according to a second modification.

FIG. 9 shows a configuration according to a second modification. The configuration according to the second modification corresponds to a configuration in which the second synthesis unit is partially modified in the configuration according to the first embodiment.

In the second modification shown in FIG. 9, the first synthesis unit 15A has the same configuration as the first synthesis unit 15A shown in FIG. 1. On the other hand, in the second modification, a second synthesis unit 15C does not include the second weighter, and includes only a second synthesizer 26A. In the second synthesizer 26A, a plurality of sub-images output from the reception unit 14 are synthesized as they are to generate the second synthetic image. In the generation unit 32, the correlation coefficient set is calculated based on the first synthetic image and the second synthetic image, and the first synthetic image is multiplied by the correlation coefficient set. Accordingly, the display image is generated.

Also in the second modification, the sidelobe components included in the display image can be reduced. According to the second modification, the second synthesis unit 15C does not need to execute weighting processing, and thus the configuration of the ultrasound diagnostic device can be simplified accordingly.

The invention claimed is:

1. An ultrasound diagnostic device comprising:
   a receiver configured to generate a plurality of sub-images for synthetic transmit aperture;
   a first synthesizer configured to generate a first synthetic image by applying a first weight distribution to the plurality of sub-images and then synthesizing the sub-images, the first weight distribution including a plurality of two-dimensionally distributed weights;
   a second synthesizer configured to generate a second synthetic image by applying a second weight distribution different from the first weight distribution to the plurality of sub-images and then synthesizing the sub-images, the second weight distribution including a plurality of two-dimensionally distributed weights; and
   a generator configured to generate a display image based on the first synthetic image and the second synthetic image, the generator including
      a calculator configured to calculate a similarity set based on the first synthetic image and the second synthetic image, and
      an adjuster configured to adjust a gain of one or both of the first synthetic image and the second synthetic image based on the similarity set to generate the display image,
   wherein the first weight distribution and the second weight distribution are applied in parallel to the same sub-images generated by the receiver.

2. The ultrasound diagnostic device according to claim 1, wherein the adjuster generates the display image by multiplying the first synthetic image by the similarity set.

3. The ultrasound diagnostic device according to claim 2, wherein the second weight distribution is a distribution that causes an increase in sidelobe components after weighting as compared with the first weight distribution.

4. The ultrasound diagnostic device according to claim 2, further comprising:
   a detector configured to apply envelope detection to the display image output from the adjuster; and
   a converter configured to apply logarithmic conversion to the display image output from the detector.

5. The ultrasound diagnostic device according to claim 1, wherein contents of the first weight distribution are different from contents of the second weight distribution.

6. The ultrasound diagnostic device according to claim 1, wherein the plurality of two-dimensionally distributed weights of the first weight distribution are different than the plurality of two-dimensionally distributed weights of the second weight distribution.

7. The ultrasound diagnostic device according to claim 1, wherein the first synthetic image and the second synthetic image, which are generated, respectively, by applying the first weight distribution to the plurality of sub-images and by applying the second weight distribution to the plurality of sub-images, have different properties from each other.

8. An image processing method comprising:
   generating a plurality of sub-images for synthetic transmit aperture;
   generating a first synthetic image by applying a first weight distribution to the plurality of sub-images and then synthesizing the sub-images, the first weight distribution including a plurality of two-dimensionally distributed weights;
   generating a second synthetic image by applying a second weight distribution different from the first weight distribution to the plurality of sub-images and then synthesizing the sub-images, the second weight distribution including a plurality of two-dimensionally distributed weights;
   calculating a similarity set based on the first synthetic image and the second synthetic image; and
   adjusting a gain of the first synthetic image based on the similarity set to generate a display image,
   the first weight distribution and the second weight distribution being applied in parallel to the same sub-images.

9. The image processing method according to claim 8, wherein the display image is generated by multiplying the first synthetic image by the similarity set.

10. The image processing method according to claim 8, wherein the second weight distribution is a distribution that causes an increase in sidelobe components after weighting as compared with the first weight distribution.

11. The image processing method according to claim 8, further comprising:
   applying envelope detection to the display image; and
   applying logarithmic conversion to the display image after applying the envelope detection.

12. The image processing method according to claim 8, wherein contents of the first weight distribution are different from contents of the second weight distribution.

13. The image processing method according to claim 8, wherein the plurality of two-dimensionally distributed weights of the first weight distribution are different than the plurality of two-dimensionally distributed weights of the second weight distribution.

14. The image processing method according to claim 8, wherein the first synthetic image and the second synthetic image, which are generated, respectively, by applying the first weight distribution to the plurality of sub-images and by applying the second weight distribution to the plurality of sub-images, have different properties from each other.

\* \* \* \* \*